United States Patent [19]
Ziemer

[11] Patent Number: 5,997,559
[45] Date of Patent: Dec. 7, 1999

[54] MICROKERATOME FOR PERFORMING LASIK SURGERY

[75] Inventor: Frank Ziemer, Port, Switzerland

[73] Assignee: Anton Meyer & Co. AG, Switzerland

[21] Appl. No.: 09/129,365

[22] Filed: Aug. 5, 1998

[30] Foreign Application Priority Data

Aug. 6, 1997 [EP] European Pat. Off. .............. 97810557

[51] Int. Cl.$^6$ ....................................................... A61F 9/00
[52] U.S. Cl. .......................................... 606/166; 606/172
[58] Field of Search .................................... 606/166, 172, 606/167, 161, 169

[56] References Cited

U.S. PATENT DOCUMENTS

| | | |
|---|---|---|
| 5,133,726 | 7/1992 | Ruiz et al. . |
| 5,342,378 | 8/1994 | Giraud et al. ............................ 606/166 |
| 5,624,456 | 4/1997 | Hellenkamp ............................ 606/172 |
| 5,861,955 | 1/1999 | Gordon .................................. 606/166 |

FOREIGN PATENT DOCUMENTS

| | | |
|---|---|---|
| 0771553 | 5/1997 | European Pat. Off. . |
| 3433581 | 3/1986 | Germany . |
| 9531143 | 11/1995 | WIPO . |

*Primary Examiner*—Michael Buiz
*Assistant Examiner*—Kevin Truong
*Attorney, Agent, or Firm*—Rothwell, Figg, Ernst & Kurz

[57] ABSTRACT

The microkeratome comprises a holder (10) with a suction ring (11) for attachment to the sclera (12) of a patient's eye (13). A suction source (20) is connected to the ring (11). A slide (30) is displaceably mounted on the holder (10) in a linear guide (22). The slide (30) has a plane frontal surface (31) including a transparent plate (32) for contacting the cornea (70) of the eye (13). The plate (32) has concentric circular marks (34) for centering on the eye (13) and for reading the diameter (D) of contact in an initial position of the slide (30). The slide (30) contains a cutting blade (51) with a cutting edge (52) that is parallel to surface (31) and oscillatable in the direction of the edge (52). Two motors (35, 57) are mounted on the slide (30) for moving the slide (30) and oscillating the blade (51). A control unit (21) is connected to the motors (35, 57) and has input means (64) for entering the measured diameter (D), the desired width (H) of the remaining hinge (68) of the flap (69) of tissue to be cut, the speed of advance of the slide (30) and the oscillating frequency of the blade (51) can be entered. The microkeratome is versatile and allows an optimization of the parameters of operation.

11 Claims, 3 Drawing Sheets

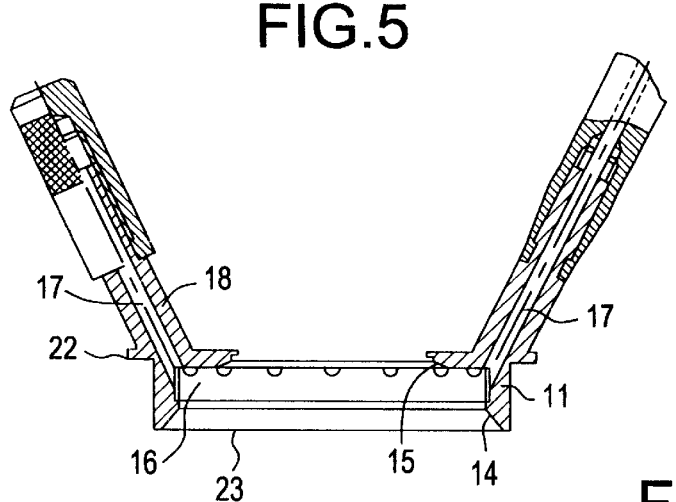
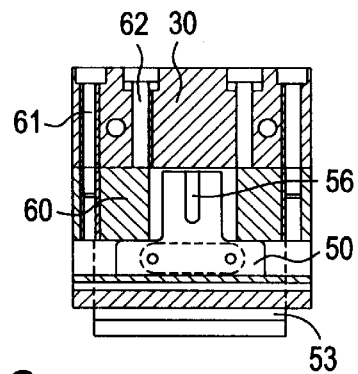
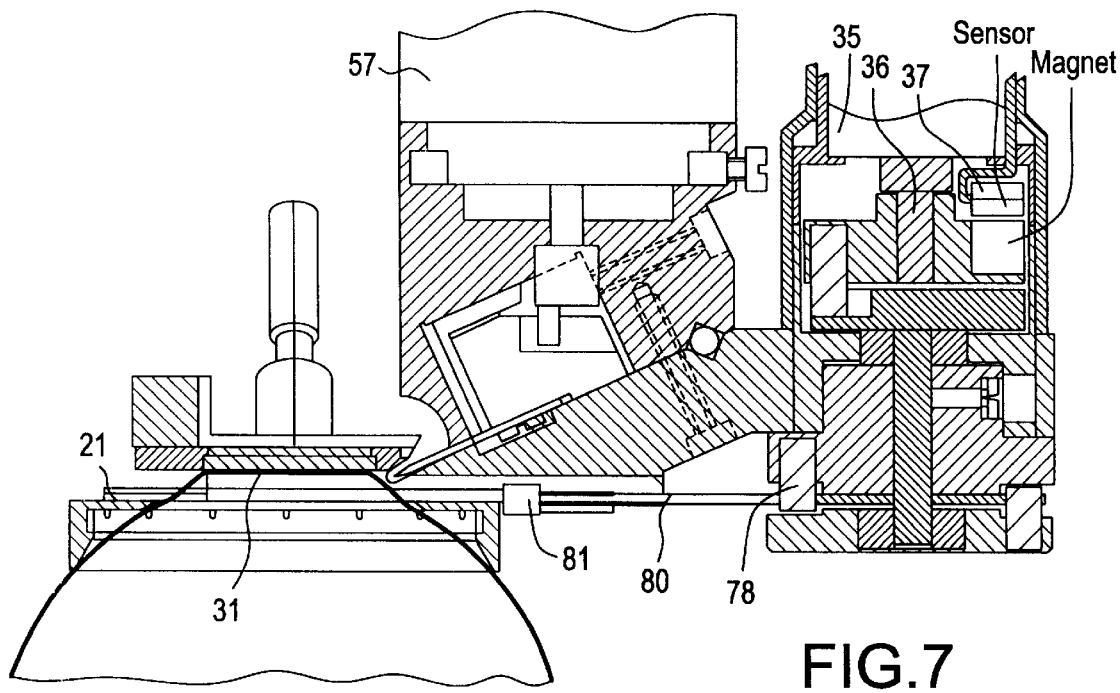
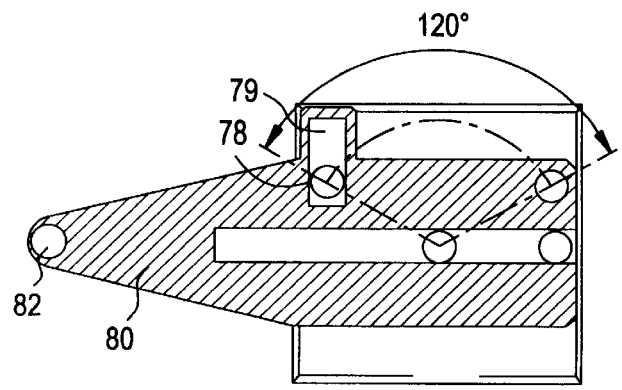

MICROKERATOME FOR PERFORMING LASIK SURGERY

FIELD OF THE INVENTION

The present invention concerns a microkeratome for performing LASIK surgery.

BACKGROUND OF THE INVENTION

LASIK (Laser Assisted In-Situ Keratomileusis) is a procedure commonly used to treat Myopia (nearsightedness), Hyperopia (farsightedness), and Astigmatism through the use of the Excimer Laser. LASIK is an operation which is performed in the Excimer Laser suite. The whole procedure is done under topical anesthesia (numbing drops) and its entire duration is seldom longer than 10 minutes. A suction ring of about 20 mm diameter is placed over the sclera (the white part of the eye) to hold the eye firmly. In performing LASIK, the surgeon first uses a microkeratome, presently with a special oscillating steel blade, to make a partial cut through the front surface of the cornea. This creates a flap of clear tissue on the front central part of the eye. So the automated microkeratome passes across the cornea to create a thin flap. This part of the operation usually takes only a few seconds. The suction ring is then retired from the eye, and the flap is lifted back to leave enough room for the usage of the Laser. The Excimer Laser, which has been previously programmed specifically for the correction of the desired amount of the visual effect, is then applied. A rapid, continuous emission of Laser pulses removes very small precise amounts of corneal tissue. Depending on the type of refractive error, this part of the surgery takes between 30 to 60 seconds. The cornea is then irrigated with saline solution, and the flap is folded back to its original position. Within minutes, the flap adheres itself to rest of the cornea and the LASIK procedure is done. In a couple of days, the cornea will be crystal clear and almost an imperceptible scar will barely be seen.

U.S. Pat. No. 5,133,726 describes a microkeratome. It comprises a holder with a suction ring for attachment to the sclera of a patient's eye. A suction source is connected to the suction ring. A slide is displaceably mounted on the holder in a linear guide. The slide has a plane frontal surface including a transparent plate for contacting the cornea of the patient's eye and slideable over the cornea in a direction parallel to the frontal surface. Attached to the slide is a flexible shaft which is driven by the motor. The end of the shaft has a threaded area which engages a pinion. The pinion drives via transmission gears a drive gear that engages in a rack on the holder to move the slide. At the extreme end of the shaft an eccentric is formed which engages a slot in a sled displaceably mounted on the slide. On the sled a steel cutting blade is mounted with a cutting edge which is parallel to the frontal surface. In operation, when the motor is started it simultaneously oscillates the blade parallel to the cutting edge and moves the slide on the holder. With this microkeratome the surgeon needs a lot of practice to position and to fix the abutting surface provided to stop the motor at the right time, i.e. at the right place. The abutting surface is to guarantee that the desired width of the remaining hinge linking the cut flap of tissue with the remaining cornea is obtained. The speed and oscillation frequency are fixed and have a fixed ratio determined by the gearing.

SUMMARY OF THE INVENTION

The problem to be solved with the present invention is to provide an improved microkeratome. This problem is solved by the combination of features disclosed hereinafter.

BRIEF DESCRIPTION OF THE DRAWINGS

Embodiments of the invention are hereinafter described with reference to the drawings, in which

FIG. 4 shows a top view of the sled with the blade (section IV—IV in FIG. 3),

FIG. 5 shows a section along the line V—V in FIG. 3 through the holder,

FIG. 6 shows a cross section through a second embodiment, and

FIG. 7 shows a plan view of the drive gear of the second embodiment.

DETAILED DESCRIPTION OF PREFERRED EMBODIMENTS OF THE INVENTION

Figure 1:
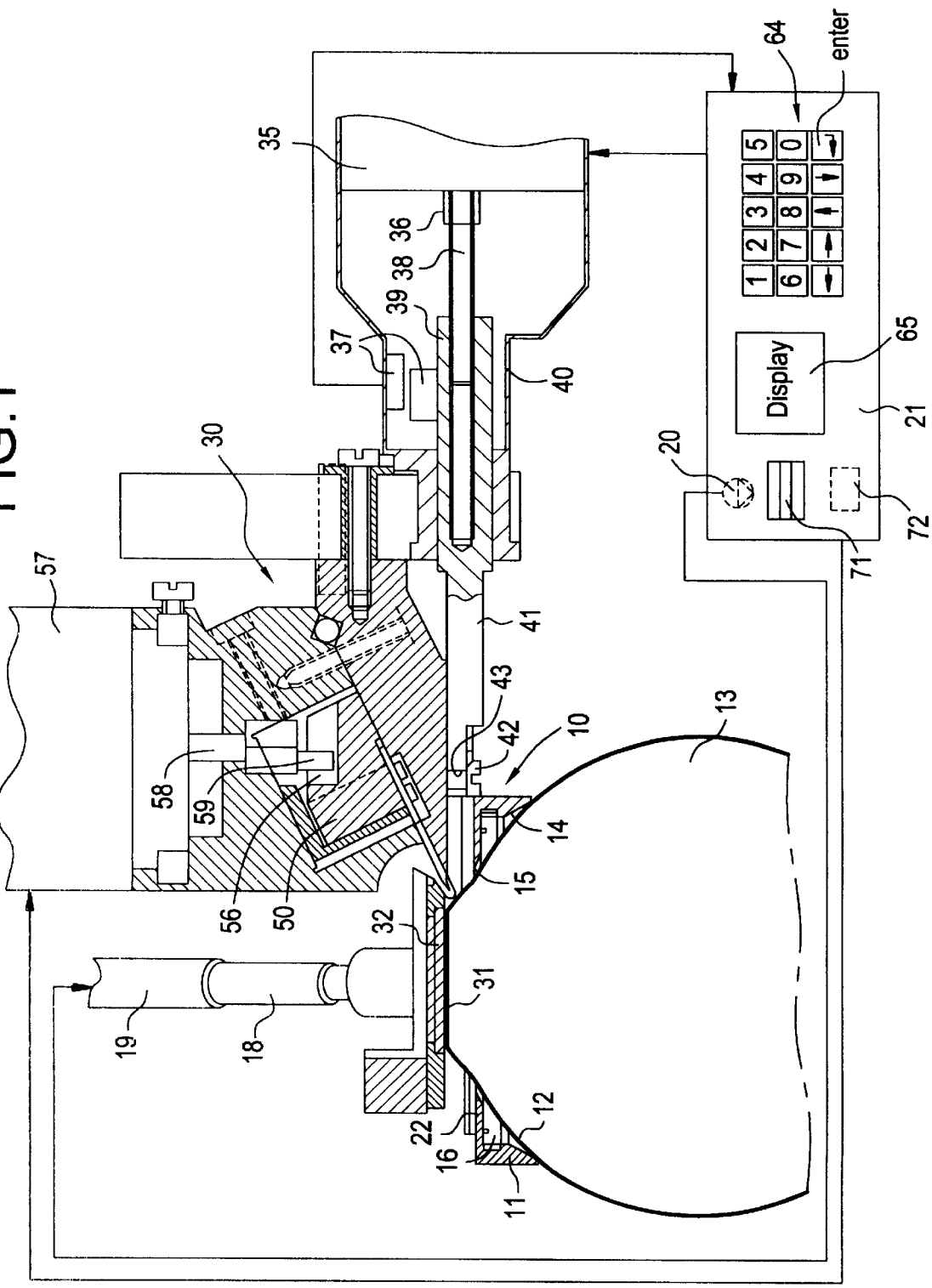
FIG. 1 shows a cross section through a first embodiment in the initial position of the slide.
Figure 2:
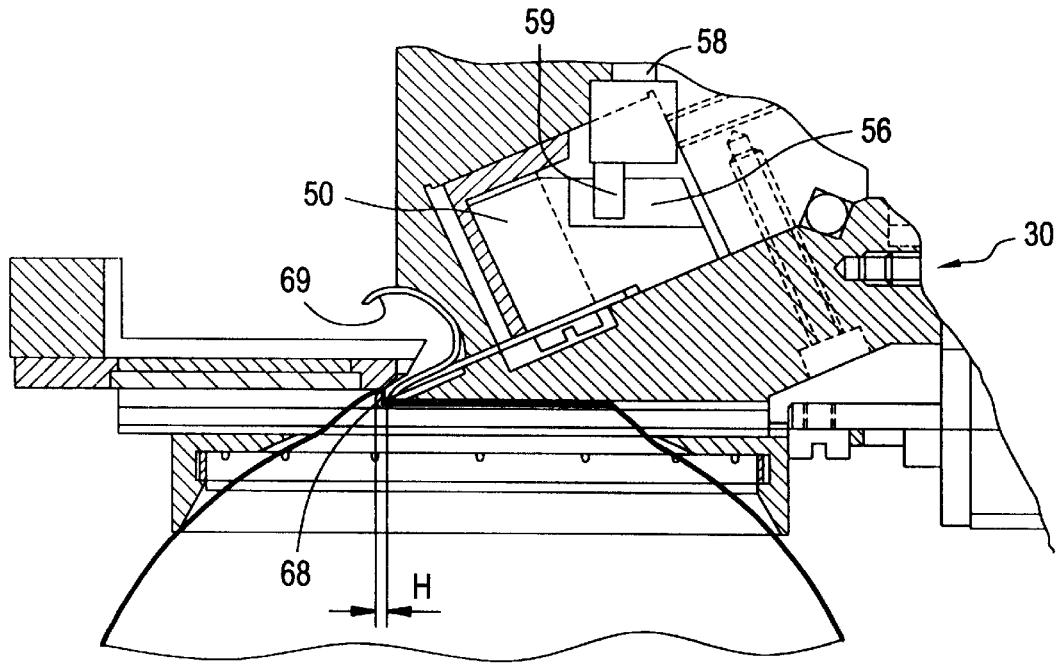
FIG. 2 shows a cross section according to FIG. 1 in the end position.

The embodiment of FIGS. 1 to 5 comprises a holder 10 with a suction ring 11 for attachment to the sclera 12 of a patient's eye 13. The ring 11 has two concentric, axially spaced conical surfaces 14, 15 and an annular recess 16 between them. A boring 17 extends from the recess 16 to a tubular stud 18 on either side of the holder 10. One of the studs 18 is closed off by a plug. The other stud 18 is connected by a tube 19 to a vacuum pump 20 in a control unit 21. On the upper side, the holder 10 has a linear dovetailed guide 22 which extends parallel to the bottom face 23 of the ring 11.

Figure 3:
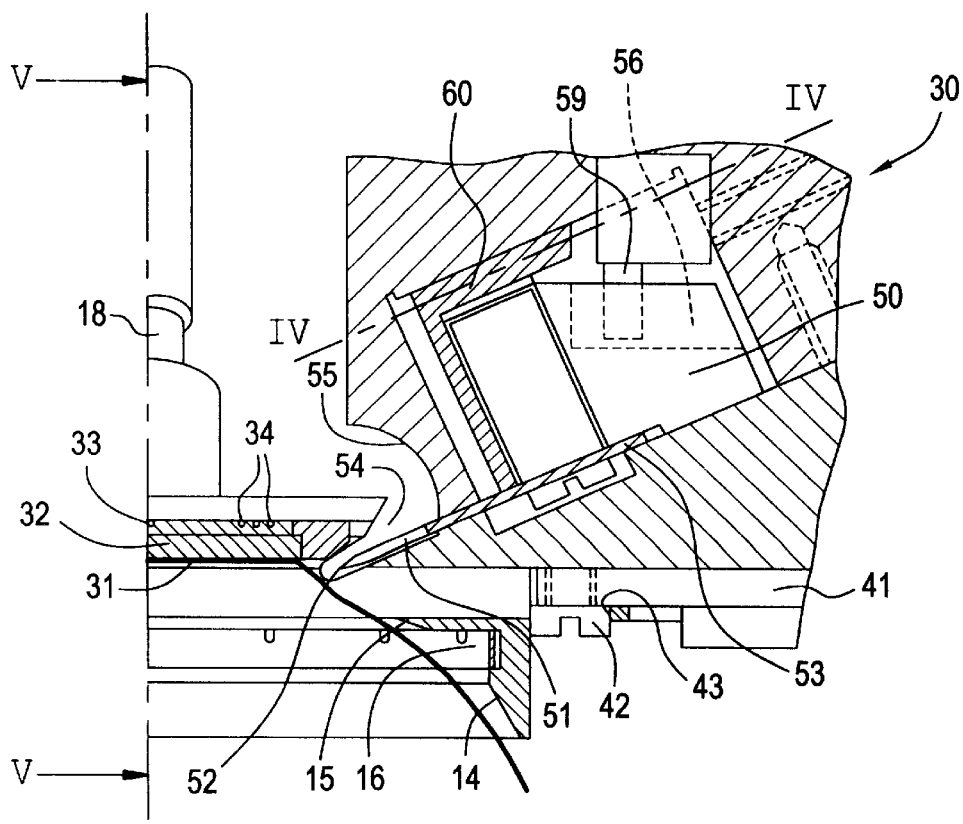
FIG. 3 shows an enlarged portion of FIG. 1

A slide 30 is guided in the guide 22 for movement relative to the holder 10. The slide 30 has a plane frontal surface 31 including a glass plate 32 for contacting the patient's eye 13. The plate 32 has crosslines 33. The center of the crosslines 33 in the initial position of the slide 30 shown in FIGS. 1 and 3 is concentric to the ring 11. Around the center of the crosslines 33 extends a number of concentric circular marks 34, e.g. with 8, 9 and 10 mm diameter. On the slide a first gearmotor 35 is detachably mounted with its axis parallel to the guide 22. The output shaft 36 of the motor 35 carries a spindle 38 which is screwed into an elongated nut 39. The nut 39 is connected to a stroke sensor 37 and is guided for axial movement in the housing 40 of the motor 35. The nut 39 is prevented from rotation relative to the housing 40. The nut 39 carries a bar 41 which at its forward free end has a pin 42 extending transverse to the axis of the motor 35 and the bar 41. The pin 42 engages in a corresponding boring 43 in the slide.

On the slide 30 a sled 50 is mounted for oscillating movement transverse to the direction of the guide 22 and parallel to the frontal surface 31. A cutting blade 51 is mounted inclined to the frontal surface 31 by about 25°. The cutting edge 52 of the blade is parallel to the frontal surface 31 and spaced downwardly from it by 0.16 mm. The blade 51 may consist of steel or of sapphire. However, in the preferred embodiment the blade is made of diamond. It is thin and vacuum brazed to a steel holder 53 of the same thickness. The blade 51 is 0.3 mm thick and 10 to 13.5 mm wide. Between the blade 51 and the glass plate 32 extends a transverse slot 54. Above the blade the slide 30 has a cylindrical concave surface 55. On its upper side the sled 50 has a groove 56 extending transverse to the direction of movement of the sled 50. On the upper side of the slide 30 a second motor 57 is detachably mounted with its axis perpendicular to the bottom face 23. The output shaft 58 of the motor 57 carries an eccentric pin 59 which engages in the groove 56. Both motors 35, 57 are controlled by the control unit 21 which contains a microprocessor. The stroke sensor 37 is connected to the unit 21 as feed-back.

As shown in FIG. 4 the sled 50 is guided in a guide block 60 which is fastened in the slide 30 by screws 61 and adjustable in the direction of the plane of the blade 53 by adjustment screws 62 to accurately adjust the thickness of the flaps 69 to be cut to 0.16 mm.

The unit 21 further contains a vacuum sensor. A key board 64 serves to enter data. A display 65 has two functions. In a first mode the data entered over the key board 64 are displaced, namely:

The diameter D of the area of contact of the plate 32 with the patient's eye 13 in the initial position of the slide 30, this diameter D being determined by the surgeon with the help of the marks 34. The diameter is generally between 8 mm and 9 mm, in rare cases up to 10 mm.

The desired width H of the remaining link or hinge 68 of the flap 69 of tissue of the cornea 70 to be cut (typically 1 to 2 mm).

The speed of advance of the slide 30 on the holder 10 which can be selected between 0.1 and 4 mm/s.

The oscillation frequency of the blade 51, i.e. the speed of the motor 57 which is selectable between 0 and 26'500 rpm.

The cutting edge 52 is spaced by 6 mm from the center of the marks 34 so that the control unit calculates the stroke S of the slide 30 according to the formula $$S = 6 \text{ mm} + D/2 - H.$$

In a second mode the display 65 displays the vacuum applied, which may also be adjustable, and the progress of the operation.

Preferably, the control unit 21 further has a sound generator 71 which emits a first audible signal when the desired vacuum is achieved, a second audible signal when the cut is finished and the slide 30 is retracted to its initial position, and a third audible signal when the pressure in the ring 11 is increased to about atmospheric pressure. This way the surgeon does not need to follow the progress of the operation on the display. The three signals are emitted at different frequencies.

The control unit further contains energy storage means 72, e.g. a large capacitor, with sufficient capacity so that a started cut can automatically be finished in case of a break in the power supply.

The described microkeratome is extremely versatile since all the essential parameters of the operation can be individually adjusted. In tests an optimum set of parameters for a given cutting blade and state of the cornea can be established. E.g. for a steel blade 51 oscillation of the blade appears to be mandatory, whereas with a diamond blade, which has a much sharper cutting edge 52 which is completely rectilinear even under an electron microscope, oscillation may not be necessary. In this case, when the microkeratome is intended for use exclusively with diamond blades 51 this blade could be mounted directly to the slide 30 and the sled 50 and motor 57 may be omitted.

In contrast to the state of the art according to U.S. Pat. Pat. No. 5,133,726 the drive of the slide 30 and the sled 50 is completely protected so that disruptions by particles falling in the gearing are avoided.

FIGS. 6 and 7 show a second embodiment which differs from the first one mainly by the drive of the slide 30. Similar parts are given the same reference numerals so that a detailed description of these parts is omitted. In the embodiment of FIGS. 6 and 7 the axis of the motor 35 is parallel to the axis of the motor 57 and perpendicular to the frontal surface 31. The shaft 36 of the motor 35 carries an eccentric pin 78 which engages a transverse slot 79 in a sliding plate 80 mounted on the slide 30 for movement parallel to the guide 21. The maximal movement of the shaft 36 from the initial position shown in FIG. 7 is 120°. The microprocessor in the control unit 21 is programmed such that the angular displacement rate of the shaft 36 is not uniform but corrected such that a uniform speed of the slide 30 over the whole stroke results. The sensor 37 in this case is an angle resolver. The plate 80 is connected to the holder 10 by a pin 81 mounted in the holder 10 and engaging a respective boring 82 in the plate 80.

In case the motor 35 is a step motor the sensor 37 may be deleted. The stroke of the slide 30 from its initial position is then determined by counting the indexing steps of the motor 35.

What I claim is:

1. A microkeratome for performing a LASIK operation, comprising a holder with a suction ring for attachment to the sclera of a patient's eye, a suction source connected to the suction ring, a slide displaceably mounted on the holder in a linear guide, the slide having a plane frontal surface including a transparent plate for contacting the cornea of the patient's eye and slideable over the cornea in a direction parallel to the frontal surface, the transparent plate having a number of concentric circular marks for centering the microkeratome on the patient's eye and for reading the diameter of the area of contact of the plate with the cornea in an initial position of the slide, the slide containing a cutting blade with a cutting edge which is parallel to the frontal surface, a first motor for moving the slide on the holder, and a control unit with input means with which at least the diameter of the area of contact and the desired width of a remaining hinge of a flap of tissue of the cornea to be cut.can be entered, the control unit controlling the amount of displacement of the slide from its initial position on the holder.

2. The microkeratome of claim 1, wherein the blade is mounted in the slide for oscillating movement in a direction parallel to the cutting edge, a second motor being mounted on the slide for oscillating the blade, and wherein in addition the oscillation frequency of the blade and the speed of advance of the slide can be pre-selected via the input means.

3. The microkeratome of claim 2, wherein the drive of the first motor contains two elements consisting of a spindle and a nut, one of the elements being mounted on a drive shaft of the first motor.

4. The microkeratome of claim 2, wherein a drive shaft of the first motor carries an eccentric pin which engages a transverse slot in a plate connected to the holder, the longitudinal direction of the slot being perpendicular to the direction of movement of the slide.

5. The microkeratome of claim 4, wherein the axes of the first and second motor are parallel and substantially perpendicular to the frontal surface.

6. The microkeratome of claim 2, wherein the control unit contains energy storage means of sufficient capacity to maintain the movements of the first and second motor for a time sufficient to finish a started cut upon interruption of the power supply to the unit.

7. The microkeratome of claim 2, wherein both motors are detachably mounted on the slide.

8. The microkeratome of claim 1, wherein the control unit further comprises a sound generator which emits a first audible signal when a predetermined subpressure is achieved in the suction ring, a second audible signal when the cut is finished and the slide is retracted to its initial position, and a third audible signal when the subpressure in the suction ring has been reduced to approximately atmospheric pressure, the three signals preferably being emitted at different frequencies.

9. The microkeratome of claim 1, wherein the control unit contains a display for displaying the data entered and the progress of the cut.

10. The microkeratome of claim 9, wherein in addition the sub-pressure applied to the suction ring is displayed in the display.

11. The microkeratome of claim 1, wherein the blade is made of diamond.

* * * * *